United States Patent [19]

Corbet et al.

[11] Patent Number: 4,883,882

[45] Date of Patent: Nov. 28, 1989

[54] PROCESS FOR THE PREPARATION OF COMPOUNDS CONTAINING A TRIAZOLE AND TETRAHYDROFURAN GROUP, AND NEW COMPOUNDS CAPABLE OF BEING EMPLOYED FOR THE PREPARATION OF THE SAID COMPOUNDS

[75] Inventors: Jean P. Corbet, Ecully; Jean M. Mas, Villeurbanne, both of France

[73] Assignee: Rhone-Poulenc Agrochimie, Lyons, France

[21] Appl. No.: 88,257

[22] Filed: Aug. 24, 1987

[30] Foreign Application Priority Data

Aug. 22, 1986 [FR] France ................... 86 12096

[51] Int. Cl.$^4$ .................................. C07D 249/08
[52] U.S. Cl. ................................ 548/262; 548/336
[58] Field of Search ...................... 548/262, 336

[56] References Cited

U.S. PATENT DOCUMENTS 4,622,334 11/1986 Reiser et al. .................. 548/262

FOREIGN PATENT DOCUMENTS 0121979 10/1984 European Pat. Off. .

*Primary Examiner*—Curtis R. Davis
*Attorney, Agent, or Firm*—Burns, Doane, Swecker & Mathis

[57] ABSTRACT

Process for the preparation of compounds containing a triazole and tetrahydrofuran group, and new compounds capable of being employed for the preparation of the said compounds.

The invention relates to a process for the preparation of 2-(1-triazolyl)methyl-2-(m-, p-dichlorophenyl)-5-OR$_1$-tetrahydrofuran compounds, R$_1$ being a lower alkyl radical, substituted if desired, by means of the following stages:

(a) isomerization of the compound of formula:
  (m-, p-diCl)Ph—C(OH)(CH$_2$Cl)—CH=CH—CH$_2$—OR$_1$
(b) grafting of a traizole ring onto the compound obtained, of formula:
  (m-, p-diCl)Ph—C(OH)(CH$_2$Cl)—CH=CH—CH$_2$—OR$_1$
(c) cyclization of the compound obtained in (b).

20 Claims, No Drawings

PROCESS FOR THE PREPARATION OF COMPOUNDS CONTAINING A TRIAZOLE AND TETRAHYDROFURAN GROUP, AND NEW COMPOUNDS CAPABLE OF BEING EMPLOYED FOR THE PREPARATION OF THE SAID COMPOUNDS

The invention relates to a process for the synthesis of compounds of formula I in which:

$R_1$ denotes the hydrogen atom or a lower alkyl, lower cycloalkyl, aryl (particularly phenyl) or aralkyl (particularly benzyl) radical, it being possible for these various radicals to be substituted, if desired, by one or more atoms or radicals such as halogen atoms and lower alkoxy, aryloxy and hydroxyl radicals, $R_2$, $R_3$ and $R_4$, which are identical or different, denote the hydrogen atom or a lower alkyl or lower cycloalkyl radical substituted, if desired, by one or more atoms or radicals such as halogen atoms and lower alkoxy, aryloxy and hydroxyl radicals, X is a halogen atom, preferably fluorine, bromine or chlorine, or an alkyl or alkoxy group containing from 1 to 12 carbon atoms, preferably from 1 to 4 carbon atoms, and, if desired, mono- or polyhalogenated (particularly a $CF_3$ group), or a cyano group in the case where $R_3$ and/or $R_4$ correspond to the hydrogen atom, n is zero or a positive integer which is smaller than 6 and is preferably 2, it being understood that when n is greater than 1, the substituents X may be either identical or different, m=0 or 1, and Z denotes a trivalent group consisting either of a =CH— group or a nitrogen atom =N—.

The term "lower" refers to an organic radical containing not more than six carbon atoms. This radical may be linear or branched.

The invention also relates to the new compounds obtained in the various stages of the process and their use for the synthesis of the compounds of formula I.

The compounds of formula I are well-known fungicidal products. They are described, in particular, in European patent applications No. 0,121,979 and/or 0,151,084.

An objective of the present invention is to provide a process for the preparation of tetahydrofurans containing triazole groups in an improved yield and under improved reaction conditions.

The process according to the invention is a process which consists of the following stages:

isomerization of the compounds of formula IV or IV$a$ in which Hal corresponds to a halogen atom and X, n, m, and $R_1$ to $R_4$ have the same meaning as in the case of formula I, in the presence of a catalyst, in homogeneous or heterogeneous phase, so as to lead to the compounds of formula III or III$a$.

This stage being followed:

either by the grafting of an imidazole or triazole ring so as to produce a compound of formula II in which X, n, m, $R_1$ to $R_4$ and W have the same meaning as in formula I, followed by the cyclization in an acidic medium so as to produce a compound of formula I, or, in the case of the compound of formula III, by the cyclization in an acidic medium so as to produce a compound of formula V, in which X, m, n and $R_1$ to $R_4$ have the same meaning as in formula I, followed by the grafting of an imidazole or triazole ring in the presence of an acid scavenger so as to produce the compound of formula I.

Although the grafting and cyclization stages may be reversed in the case of the compound of formula III, it is preferable, nevertheless, to proceed in the order which follows:

(a) isomerization, (b) grafting, (c) cyclization.

Thus, in the description to follow, unless stated otherwise, the various stages will be described in this order. It is obvious, however, that the operating conditions are identical when the order of stages (b) and (c) is reversed, although this route is less advantageous.

Among the catalysts which may be employed to ensure the isomerization, the following transition metals may be mentioned advantageously: ruthenium, cobalt, palladium, nickel, rhodium, iridium and platinum.

These catalysts may operate in heterogeneous form in the metallic state, and in this case they are deposited on a suitable inert support such as carbon black. Preferably, they can also function in homogeneous catalysis in the form of complexes which, in addition to the transition metal, include one or several appropriate ligands (phosphine, carbonyl) and one or more hydride molecules.

Unexpectedly, this reaction takes place with excellent yields, especially in the case of ruthenium-based catalysts, whereas the person skilled in the art might have normally expected interference from a reaction resulting from the shift of the double bond towards the carbon bearing the hydroxyl group (isomerization of the allylic alcohol) or epoxy group.

The reaction may be carried out in bulk or in the presence of a protonic or aprotic solvent.

Among aprotic solvents there may be mentioned saturated aliphatic hydrocarbons such as n-pentane, isopentane, 2-methylhexane, 2,2,5-trimethylhexane, aromatic hydrocarbons such as benzene, toluene and ethylbenzene, saturated aliphatic ethers such as tetrahydrofuran and isopentyl ether, aromatic ethers such as benzyl ethyl ether, saturated aliphatic or aromatic ketones such as methyl ethyl ketone, methyl isobutyl ketone and acetophenone, saturated aliphatic or aromatic halogenated hydrocarbons such as fluorobenzene, 1-chloro-2-methylpropane and isobutyl chloride, and saturated aliphatic or aromatic esters such as isobutyl isobutyrate, ethyl acetate and methyl benzoate. All these solvents may be present by themselves or mixed.

Among protonic solvents there may be mentioned saturated aliphatic or aromatic alcohols such as methanol, isopropanol and phenol, and saturated aliphatic or aromatic acids such as acetic acid and benzoic acid. It is also possible to use an inorganic acid mixed with an above-mentioned organic solvent with which it is miscible, e.g. hydrochloric acid in methanol. In this case, the products of formula V are obtained directly. All these solvents may be present mixed or by themselves.

Preference among these solvents is given to aromatic hydrocarbons or saturated lower aliphatic alcohols. When the reaction is carried out in the presence of a solvent, the dilution of the reaction product will be particularly between 0.5% and 99% by weight based on the total weight of the solution, and preferably between 5 and 50%.

The quantity of catalyst employed will preferably be between 0.0005 and 0.1 mole per mole of compound of formula IV or IV$a$.

The reaction temperature may vary within a wide range, e.g. between −20° C. and the decomposition temperature of the catalyst. Nevertheless, a satisfactory compromise between the reaction time and industrial operating conditions results in preference being given to a temperature range from 0° C. to 100° C., advantageously between 10° C. and 80° C.

The pressure is generally between 1 and 10 atmospheres (0.1 to 1 MPa).

In the case where the groups $R_3$ and $R_4$ both correspond to hydrogen atoms, a preferred synthetic route to the compound of formula IV or IVa consists in hydrogenating the compound of formula VI, in which X, n, m, $R_1$, $R_2$ and Hal have the same meaning as in formula I or IV, with an equimolar quantity of hydrogen using a suitable catalyst, poisoned if desired and chosen from the following catalysts: palladium, ruthenium, Raney nickel, platinum, rhodium, and preferably palladium, poisoned if desired (pyridine, quinoline), which yields specifically the cis olefin.

As before, this reaction may be performed in homogeneous or heterogeneous phase.

The preferred choice will be metallic palladium deposited onto an inert support such as carbon black, calcium carbonate or barium sulphate.

While it is not an essential requirement, the hydrogenation reaction may advantageously be carried out in a polar protonic or aprotic solvent, which is identical with those employed for the isomerization stage, apart from the fact that halogenated hydrocarbons cannot be employed in the case of Raney nickel.

The dilution of the compound of formula VI is preferably between 1 and 80% by weight or, better, 5% and 40%, based on the total weight of solution.

Similarly, while the molar proportion of catalyst in relation to the compound of formula VI may vary considerably, for obvious industrial reasons it will be preferable for the catalyst to be employed in a molar proportion of between 0.01 and 0.5% relative to the compound of formula VI.

The reaction takes place at temperatures of between −20° C. and 150° C., preferably between 10° and 80° C., and at a pressure which is generally between 1 and 10 atmospheres (0.1 MPa and 1 MPa).

The compound of formula VI may be obtained by the addition of the organomagnesium derivative of formula

$R_2-(OR_1)CH-C\equiv C-Mg-Br$     VII with a haloacetophenone of formula     VIII

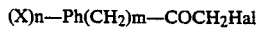

$(X)n-Ph(CH_2)m-COCH_2Hal$

The reaction may, for example, be performed in tetrahydrofuran in a known manner, or in a mixture of a hydrocarbon such as toluene and an ether such as tetrahydrofuran.

In the case where at least one of the groups $R_3$ and $R_4$ does not correspond to the hydrogen atom, the following synthetic route can be employed: addition of an organomagnesium derivative of formula $R_4MgX$ to the compounds of general formula VI, in the presence or absence of copper iodide followed, if desired, by the addition of an alkyl halide $R_3X$ in a solvent such as tetrahydrofuran. When stopping with the addition of $R_4MgX$, it is quite obvious that this addition stage is followed by a hydrolysis.

Compound IVa is produced by the action of an alcoholic base (methanolic sodium hydroxide or potassium hydroxide) with compound IV (the reaction generally takes place at a temperature between −10° C. and 50° C. in the presence of 1 to 2 molar equivalents of alcoholate per mole of compound of formula IV).

The grafting stage is advantageously carried out in the presence of an acid-scavenger, in an anhydrous or nonanhydrous medium, in a solvent which is inert under the reaction conditions, generally between 50° and 180° C. and preferably at a temperature close to the boiling point of the solvent. As acid-scavengers there may be mentioned inorganic bases such as, e.g., sodium or potassium hydroxide, alkali metal or alkaline-earth metal carbonates, nitrogenous bases such as triethylamine, quaternary amines such as tetrabutylammonium hydroxide or phosphonium hydroxides. Solvents which are advantageously employed are polar aprotic solvents such as, e.g., dimethylformamide, dimethylacetamide, dimethyl sulphoxide, acetone, methyl ethyl ketone, methyl isobutyl ketone, acetonitrile, Nmethylpyrrolidone or polar protonic solvents, such as methanol or propanol. If desired, this reaction may be carried out in the presence of an appropriate catalyst. Phase transfer catalysts such as, e.g., quaternary ammonium derivatives such as tetrabutylammonium chloride, may be mentioned as a catalyst which can be employed.

The grafting reaction is preferably carried out with a molar excess, preferably between 1.05 and 1.5, of triazole or imidazole derivative.

When a solvent is employed, it will be preferable to operate in a dilute medium containing 1% to 70% by weight of compound of formula III or IIIa or V relative to the total solution.

The acid-scavenger is present in a quantity which is at least stoichiometrically equal on an equivalent basis to the labile hydrogen atom of the triazole or imidazole. A molar equivalent ratio of between 1 and 2.5 will generally be satisfactory.

It is obvious that the triazole or imidazole salt derivative may be prepared separately and, in this case, there is no need for an acid-scavenger to be present for the grafting reaction. This preparation is performed in an anhydrous or nonanhydrous medium, in a solvent under the same operating conditions as those described in the case of in situ formation of the triazole or imidazole salt derivative.

Insofar as the grafting stage is concerned, it is advantageous, and this constitutes one of the characterizing features of the invention, to pass through an epoxide intermediate of formula IIIa in which X, n, m and $R_1$ to $R_4$ have the same meaning as in formula I, either by treating the compound of formula III with an alcoholic base such as methanolic potassium hydroxide or sodium hydroxide (the reaction generally takes place at a temperature of between −10° C. and 50° C., in the presence of 1 or 2 molar equivalents of alcoholate per mole of compound of formula III), or by isomerization under operating conditions which are identical with those for the chlorohydrin of formula IV of the epoxide of formula IVa, produced by treating the compound of formula IV with a base under conditions which are identical with those indicated above.

The intermediate product of formula IIIa may be isolated by distillation or may, on the contrary, be directly subjected to the stage in which the imidazole or triazole ring is actually grafted. In this case, the reaction may be carried out at temperatures below 130° C. and above 50° C., if desired in a suitable solvent which is preferably polar, such as dimethyl formamide or dimethyl sulphoxide or alcohols from $C_1$ to $C_4$.

The molar ratio of the triazole or imidazole salt derivative to the compound of formula (IIIa) is, as before, between 1.05 and 1.5. As before, the imidazole or triazole salt derivative may be prepared in situ by a reaction with the corresponding base.

Insofar as the cyclization stage is concerned, the reaction takes place in an acidic medium.

The acidic catalyst employed in this reaction may be a protonic or aprotic acid which is soluble or insoluble. As protonic acids there may be mentioned hydrochloric, sulphuric, trifluoroacetic, perchloric, benzenesulphonic, toluenesulphonic and methanesulphonic acids. As aprotic acids there may be mentioned Lewis acids such as $BF_3$, $AlCl_3$ and $SnCl_4$. Solid resins such as sulphonic resins may also be employed.

0.1 to 2 molar equivalents of acids will preferably be employed per mole of compound of formula II or III.

The reaction is usually carried out merely by heating the reactants shown. The temperature is generally between 10° C. and 100° C. or, if a solvent is present, between 10° C. and the boiling point of the solvent in question. The solvent employed may be, in particular, a halogenated or unhalogenated aliphatic, alicyclic or aromatic hydrocarbon, an ether, or an alcohol such as that of formula $R_1OH$.

An especially preferred alternative form of the process according to the invention, aimed at obtaining the compounds of formula I in which $R_1$ denotes a lower. alkyl, lower cycloalkyl, aryl or aralkyl radical, the said radicals being substituted as indicated in the general definition of radical $R_1$ at the beginning of the description, consists in reacting a compound of formula II or III, in which $R_1$ corresponds to the hydrogen atom or a lower alkyl, lower cycloalkyl, aryl or aralkyl radical, with a compound of formula $R_5OH$, in which $R_5$ corresponds to a lower alkyl, lower cycloalkyl, aryl or aralkyl radical, the said radicals being substituted as indicated in the general definition of radical $R_1$ at the beginning of the description, in the presence of an abovementioned acidic catalyst and under the operating conditions which have already been listed in the description of the cyclization stage.

This reaction leads to the desired product in an excellent yield.

In general, the reaction is carried out with a molar excess, preferably from 1.05 to 10 and advantageously from 2 to 6, of compound of formula $R_5OH$.

In the case where $R_1$ is the hydrogen atom and when starting with the compound of formula IV or IVa, the isomerization stage leads to cyclization, and the isomerization and cyclization stages are then interlinked. The grafting stage is carried out subsequently.

Whatever the process employed, the compound of formula I which is formed at the end of reaction is isolated from the reaction mixture by any means which is known per se such as, e.g., distillation of the solvent or crystallization of the product from the reaction mixture, or by filtration, and, if need be, this compound is purified by normal methods such as recrystallization from a suitable solvent.

The invention also relates to the compounds of formula II, III, IIIa, IV, IVa, VI, VII and VIII in which X, $R_1$ to $R_4$, m, n, Hal and Z have the same meaning as in the compound of formula I. These compounds are employed for the preparation of the compound of formula I in the same way as the compound of formula V.

The examples which follow illustrate the invention:

Example 1: Preparation of 2-(2,4-dichloro-1-phenyl)-2-(1-triazolylmethyl)-5-trifluoroethoxytetrahydrofuran 2-(2,4-Dichloro-1-phenyl)-5-methoxy-1-triazolyl-4-penten-2-ol (0.984 g, 3 mmol) and trifluoroethanol (3 ml) are introduced into a 10-ml round flask under an inert atmosphere. Gaseous HCl is introduced at approximately 75° C. The methanol formed is removed by distillation. After 10 h, the mixture is cooled, neutralized, extracted and filtered. The residue (0.68 g; 1.71 mmol) melts at 162° C.

Yield based on starting material: 57.2%.

Example 2: Preparation of 2-(2,4-dichloro-1-phenyl)-5-methoxy-1-triazolyl-4-penten-2-ol 1,2,4-Triazole (0.828 g; 11.9 mmol), sodium methylate (0.54 g; 10.0 mmol) and dry N,N-dimethylformamide (2.5 ml) are introduced into a 10-ml round flask under an inert atmosphere. After 15 minutes 1-(2,4-dichloro-1-phenyl)-1-(3-methoxy-2-propen-1-yl)oxirane (cis and trans isomers) (2.59 g; 10.0 mmol) is added in anhydrous DMF (2.5 ml). After 5 h at 118° C., the mixture is cooled and $CH_2Cl_2$ (25 ml) is added, and the mixture is washed with water, extracted and dried. The dry extract is an oily residue: 3.37 g. After purification a pure oily product (2.14 g; 6.52 mmol) is obtained.

Yield: 65%, based on starting material.

Example 3: Preparation of 1-(2,4-dichloro-1-phenyl)-1(3-methoxy-2-propen-1-yl)oxirane (cis and trans isomers)

A solution of 1-chloro-2-(2,4-dichloro-1-phenyl)-5-methoxy-4-penten-2-ol (1.19 g; 4.03 mmol) is introduced into a 25-ml round flask under an inert atmosphere with methanol (2 ml) and $RuH_2(PPh_3)_4$ (46.27 mg; 0.04 mmol) during 1 h at 50° C. The mixture is cooled and concentrated and the catalyst is filtered off. A yellow oil (1.19 g; 4.03 mmol) is obtained.

Yield: 100%, based on starting material.

Example 4: Preparation of 1-chloro-2-(2,4-dichloro-1-phenyl)-5-methoxy-4-penten-2-ol 1-Chloro-2-(2,4-dichloro-1-phenyl)-5-methoxy-3-pentyn-2-ol (40.2 g; 136.93 mmol), methanol (300 ml) and palladium at a concentration of 5% on charcoal (218.3 mg; 0.102 milligram-atom) are introduced into a 1-l round flask under an inert atmosphere. Hydrogen is introduced. After 2 h 30 min at 22° C. the hydrogen is purged out and the solution is filtered and concentrated.

Yield: 98% of oily residue.

Example 5: Preparation of 1-chloro-2-(2,4-dichloro-1-phenyl)-5-methoxy-3-pentyn-2-ol Magnesium (4 g; 0.164 mol) and THF (8 ml) are introduced into a 100-ml round flask under an inert atmosphere. Bromoethane (16.34 g; 0.149 mol) in THF (60 ml) is added while the temperature is maintained at 25° C. for 1 h. At the end of addition, THF (40 ml) is added. The magnesium derivative produced in this manner is filtered off under an inert atmosphere and is then poured onto a solution of 3-methoxy-1-propyne (10.57 g; 0.15 mol) in THF (50 ml) placed in a 250-ml round flask under an inert atmosphere. The temperature is maintained at 20°-25° C. When the addition is complete, 2,4,2'-trichloroacetophenone (22.35 g; 0.1 mol) is added in THF (25 ml). The temperature is maintained at 22°-24° C. When the addition is complete, acetic acid (9 g; 0.15 mol) is added and the solution is concentrated down to a volume of 100 ml. Methylcyclohexane (75 ml) is then added, and the solution is washed, concentrated and recrystallized from cyclohexane. A white crystalline product (21.45 g; 73.16 mmol), which melts at 98° C., is obtained.

Yield: 73%.

3-Methoxy-1-propyne is prepared according to W. Reppe, Annalen, 596, 74, 1955.

Example 6: Preparation of 2-(2,4-dichloro-1-phenyl)-2-(1-chloromethyl)-5-methoxytetrahydrofuran 1-Chloro-2-(2,4-dichloro-1-phenyl)-5-methoxy-4-penten-2-ol (0.860 g; 2.9 mmol), dry toluene (5 ml) and p-toluenesulphonic acid (0.05 g; 0.29 mmol) are introduced into a 25-ml round flask under an inert atmosphere. After 30 minutes the mixture is cooled, washed with water, dried and concentrated. A 95% pure oily residue (0.6 g) is obtained.

Example 7: Preparation of 2-(2,4-dichloro-1-phenyl)-2-(1-triazolylmethyl)-5-methoxytetrahydrofuran 2-(2,4-Dichloro-1-phenyl)-2-(1-chloromethyl)-5-methoxytetrahydrofuran (0.3 g; 1 mmol) as a solution in N-methylpyrrolidone (3 ml) and sodium triazolate (0.092 g; 1 mmol) are introduced into a 10-ml round flask under an inert atmosphere. After 6 h at 160° C. the mixture is cooled and a crude product (0.414 g) is obtained and found to contain 74.21 mg of compound.

Yield: 22.6%

Example 8: Preparation of 2-(2,4-dichloro-1-phenyl)-2-(1-triazolylmethyl)-5-hydroxytetrahydrofuran 2-(2,4-Dichloro-1-phenyl)-5-methoxy-1-triazolyl-4-penten-2-ol (0.131 g; 0.4 mol) in N,N-dimethylformamide (0.5 ml) and a 2N solution of HCl (2 ml) are introduced into a 10-ml round flask. After 2 h 30 min at 60° C., the mixture is neutralized. After removal of the supernatant, washing with water and drying, a crude reaction product (0.124 g) is obtained and this, after being taken up with petroleum ether, crystallizes to yield, after filtration and drying, the hydroxyl derivative (0.107 g; 0.34 mmol) in the form of an 80/20 mixture of the two diastereoisomers.

FORMULAE OF THE COMPOUNDS

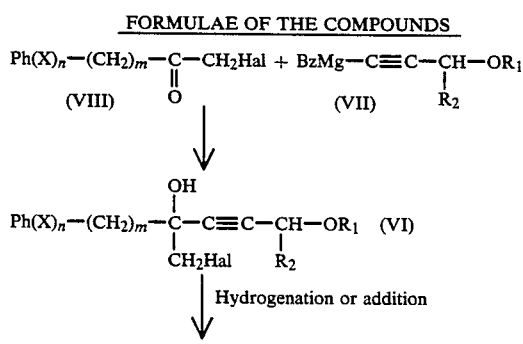

FORMULAE OF THE COMPOUNDS -continued

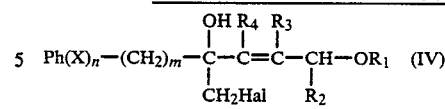

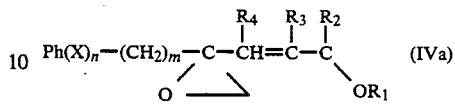

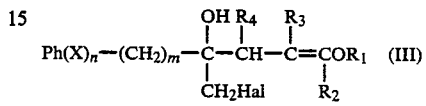

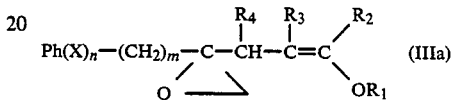

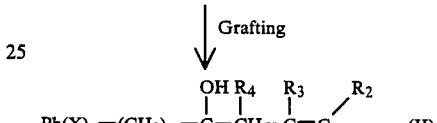

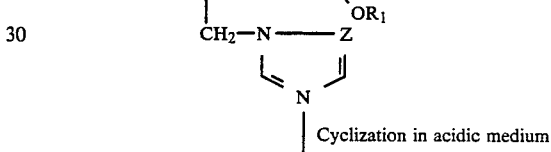

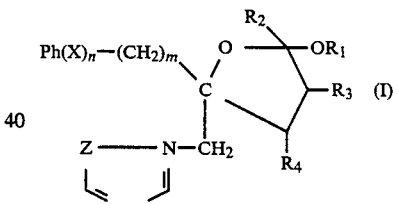

We claim:

1. A process for the synthesis of compounds of formula I,

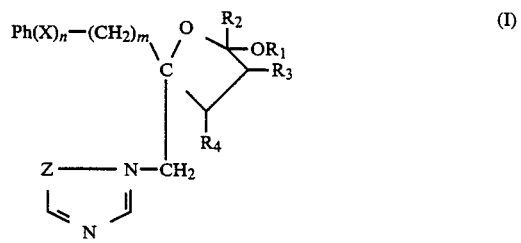

in which:

$R_1$ denotes the hydrogen atom or a lower alkyl, lower cycloalkyl, aryl or aralkyl radical, wherein said radical is unsubstituted or substituted by one or more atoms or radicals, $R_2$, $R_3$ and $R_4$, which are identical or different denote a hydrogen atom or a lower alkyl or lower cycloalkyl radical, wherein said radical is unsubstituted or substituted by one or more atoms or radicals, X is a halogen atom or an alkyl or alkoxy group containing from 1 to 12 carbon atoms which is unsubstituted or substituted with a mono- or polyhalogenated or a cyano group in the case where one or more of $R_3$ and $R_4$ correspond to the hydrogen atom, n is zero or a positive integer which is smaller than 6, it being understood that when n is greater than 1, the substituents X may be either identical or different, m equals 0 or 1, and Z denotes a trivalent group consisting either of a =CH— group or a nitrogen atom =N—, the process comprising:

isomerizing compounds of formula IV or IVa $$Ph(X)_n-(CH_2)_m-\overset{\overset{\displaystyle OH}{|}}{\underset{\underset{\displaystyle CH_2Hal}{|}}{C}}-\overset{\overset{\displaystyle R_4}{|}}{C}=\overset{\overset{\displaystyle R_3}{|}}{\underset{\underset{\displaystyle R_2}{|}}{C}}-CH-OR_1 \quad (IV)$$

$$Ph(X)_n-(CH_2)_m-\overset{\overset{\displaystyle R_4}{|}}{\underset{\diagup \quad \diagdown}{\underset{O \longrightarrow}{C}}}-\overset{\overset{\displaystyle R_3}{|}}{CH}=\overset{\overset{\displaystyle R_2}{|}}{C}\diagdown_{OR_1} \quad (IVa)$$

in which Hal corresponds to a halogen atom and X, n, m, and $R_1$ to $R_4$ have the same meaning as in the case of formula I, in the presence of a catalyst, in homogeneous or heterogeneous phase, so as to lead to the compounds of formula III or IIIa, $$Ph(X)_n-(CH_2)_m-\overset{\overset{\displaystyle OH}{|}}{\underset{\underset{\displaystyle CH_2Hal}{|}}{C}}-\overset{\overset{\displaystyle R_4}{|}}{CH}-\overset{\overset{\displaystyle R_3}{|}}{\underset{\underset{\displaystyle R_2}{|}}{C}}=COR_1 \quad (III)$$

$$Ph(X)_n-(CH_2)_m-\overset{\overset{\displaystyle R_4}{|}}{\underset{\diagup \quad \diagdown}{\underset{O \longrightarrow}{C}}}-\overset{\overset{\displaystyle R_3}{|}}{CH}-\overset{\displaystyle R_2}{C}\underset{\diagdown OR_1}{\diagup} \quad (IIIa)$$

this stage being followed:

either by grafting an imidazole or triazole ring to produce a compound of formula II $$Ph(X)_n-(CH_2)_m-\overset{\overset{\displaystyle OH}{|}}{\underset{\underset{\displaystyle CH_2-N-Z}{|}}{C}}-\overset{\overset{\displaystyle R_4}{|}}{CH}-\overset{\overset{\displaystyle R_3}{|}}{C}=\overset{\displaystyle R_2}{C}\underset{\diagdown OR_1}{\diagup} \quad (II)$$

in which X, n, m, $R_1$ to $R_4$ and Z have the same meaning as in formula I, followed by cyclizing the resulting compound in an acidic medium to produce a compound of formula I, or, in the case of the compound of formula III, cyclizing a compound of formula III in an acidic medium to produce a compound of formula V, $$Ph(X)_n-(CH_2)_m\diagdown_{HalCH_2}\overset{\displaystyle R_2}{\underset{\underset{\displaystyle R_4}{|}}{\overset{O \diagup \diagdown OR_1}{\underset{| R_3}{}}}} \quad (V)$$

in which X, m, n and $R_1$ to $R_4$ have the same meaning as in formula I, followed by grafting an imidazole or triazole ring in the presence of an acid scavenger to produce the compound of formula I.

2. The process according to claim 1, wherein the isomerization catalyst is chosen from the group consisting of: ruthenium, cobalt, palladium, nickel, rhodium, iridium and platinum.

3. The process according to claim 2, wherein the molar proportion of catalyst relative to the compounds of formula IV or IVa is between 0.0005 and 0.1.

4. The process according to claim 1, wherein the isomerization reaction takes place in the presence of a solvent and where, preferably, the quantity of compounds of formulas IV or IVa relative to the solvent is between 5 and 50% by weight.

5. The process according to claim 1, wherein the temperature of the isomerization reaction is between 10° C. and 80° C.

6. The process according to claim 1, wherein the grafting stage is carried out by means of an imidazole or triazole salt derivative formed in situ, and wherein the molar ratio of said derivative relative to the compound of formula III or IIIa or V is between 1.05 and 1.5.

7. The process according to either of claims 1 or 6, wherein the grafting image stage reaction is carried out in the presence of a solvent and wherein the quantity of compounds of formula III or IIIa or V based on the solvent is between 1 and 70% by weight.

8. The process according claims 1 or 6, wherein the temperature of the grafting stage reaction is close to the boiling point of the solvent.

9. The process according to claim 1, wherein the grafting stage reaction is carried out in two half-stages (1) and (2):
(1) forming a compound of formula IIIa in which X, $R_1$ to $R_4$, m and n have the same meaning as in the case of the compound of formula I, by reacting an alcoholic base with the compound of formula III or by isomerizing the compound of formula IVa, and
(2) grafting an imidazole of triazole ring using (a) an imidazole or triazole salt derivative formed in situ where the molar ratio of said derivative relative to the compound of formula III or IIIa is between 1.05 and 1.5, (b) a solvent during the grafting reaction wherein the quantity of the compounds of formula III or IIIa or V used on the solvent is between 1 and 70% by weight, or (c) where the temperature of the grafting stage reaction is close to the boiling point of the solvent.

10. The process according to claim 9, wherein the reaction with the alcoholic base is carried out in the presence of 1 to 2 molar equivalents of base per mole of compound of formula III.

11. The process according to claim 9 or 10, wherein the reaction temperature in the half-stage (1) is between −10° C. and 50° C.

12. The process according to claim 9, wherein the reaction temperature in the half-stage (2) is between 50° C. and 130° C.

13. The process according to claim 1, wherein the cyclization reaction is carried out in the presence of 0.1 to 2 molar equivalents of acids per mole of compound of formula II or III.

14. The process according to either of claims 1 or 13, wherein the reaction temperature is between 10° C. and 100° C.

15. The process according to claim 1, wherein the compounds of formula I, in which $R_1$ denotes a lower alkyl, lower cycloalkyl, aryl or aralkyl radical, substituted as indicated in claim 1, are produced by reaction of a compound of formula II or III in which $R_1$ corresponds to the hydrogen atom or to a lower alkyl, lower cycloalkyl, aryl or aralkyl radical, with a compound of formula $R_5OH$, in which $R_5$ denotes a lower alkyl, lower cycloalkyl, aryl or aralkyl radical substituted as indicated in claim 1, in the presence of an acidic catalyst wherein the cyclization reaction is carried out in the presence of 0.1 to 2 molar equivalents of acids per mole of compound of formula II or III or wherein the reaction temperature is between 10° C. and 100° C.

16. The process according to claim 15, wherein the molar ratio of the compound of formula $R_5OH$ relative to the compound of formula II or III is between 1.05 and 10.

17. The process according to claim 1, wherein the cyclization of the compound of formula III or IIIa is carried out during the isomerization stage in the case where $R_1$ corresponds to the hydrogen atom.

18. The process according to claim 4, wherein the quantity of compounds of formula IV or IVa relative to the solvent is between 5 and 50% by weight.

19. The process according to claim 14 involving the use of a solvent at a temperature between 10° C. and the boiling point of the selected solvent.

20. A process for the synthesis of compounds of formula I,

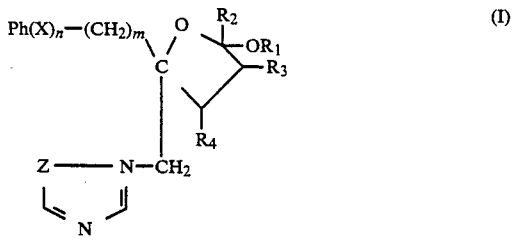

in which:
$R_1$ denotes the hydrogen atom or lower alkyl, lower cycloalkyl, phenyl or aralkyl radical, wherein said radical may be unsubstituted or substituted by one or more halogen atoms or lower alkoxy, aryloxy or hydroxyl radicals, $R_2$, $R_3$ and $R_4$, which are identical or different, denote a hydrogen atom or a lower alkyl or lower cycloalkyl radical, wherein said radical is unsubstituted or substituted by one or more halogen atoms or lower alkoxy, aryloxy or hydroxyl radicals, X is a fluorine, bromine or chlorine atom or an alkyl or alkoxy group containing 1 to 4 carbon atoms which is unsubstituted or substituted with a $CF_3$ group or a cyano group in the case where one or more of $R_3$ and $R_4$ correspond to the hydrogen atom, n is zero or two, it being understood that when n is two, the substituents X may be either identical or different, m equals zero or one, and Z denotes a trivalent group consisting either of a =CH— group or a nitrogen atom =N—, the process comprising: isomerizing compounds of formula IV or IVa

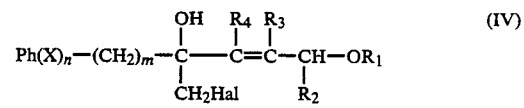

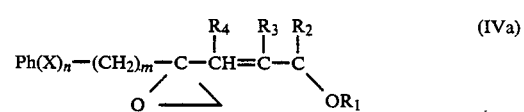

in which Hal corresponds to a halogen atom and X, n, m, and $R_1$ to $R_4$ have the same meaning as in the case of formula I, in the presence of a catalyst, in homogeneous or heterogeneous phase, so as to lead to the compounds of formula III or IIIa,

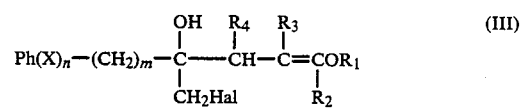

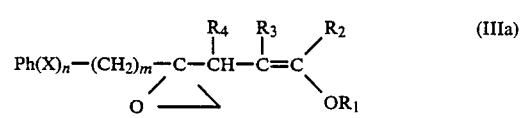

this stage being followed:
either by grafting an imidazole or triazole ring to produce a compound of formula II

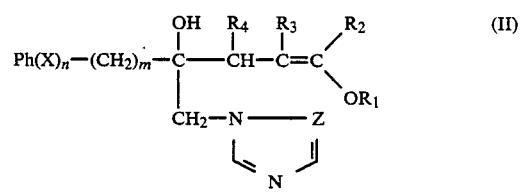

in which X, n, m, $R_1$ to $R_4$ and Z have the same meaning as in formula I, followed by cyclizing the resulting compound in an acidic medium to produce a compound of formula I, or, in the case of the compound of formula III, cyclizing a compound of formula III in an acidic medium to produce a compound of formula V,

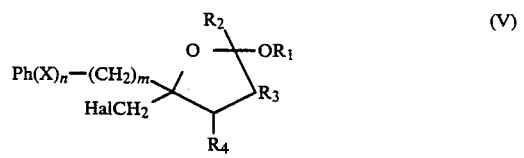

in which X, m, n, and $R_1$ and $R_4$ have the same meaning as in formula I, followed by grafting an imidazole or triazole ring in the presence of an acid scavenger to produce the compound of formula I.

* * * * *